(12) United States Patent
Leung

(10) Patent No.: US 10,334,878 B2
(45) Date of Patent: Jul. 2, 2019

(54) HANDHELD VAPORIZING DEVICE

(71) Applicant: Nuryan Holdings Limited, San Mateo, CA (US)

(72) Inventor: David Chung Sing Leung, San Mateo, CA (US)

(73) Assignee: NURYAN HOLDINGS LIMITED, San Mateo, CA (US)

( * ) Notice: Subject to any disclaimer, the term of this patent is extended or adjusted under 35 U.S.C. 154(b) by 148 days.

(21) Appl. No.: 14/718,551

(22) Filed: May 21, 2015

(65) Prior Publication Data
US 2015/0335074 A1 Nov. 26, 2015

Related U.S. Application Data

(60) Provisional application No. 62/001,972, filed on May 22, 2014.

(51) Int. Cl.
*A24F 47/00* (2006.01)
*F22B 1/28* (2006.01)
(Continued)

(52) U.S. Cl.
CPC ......... *A24F 47/008* (2013.01); *A61M 11/044* (2014.02); *A61M 15/06* (2013.01); *F22B 1/284* (2013.01); *H05B 1/0297* (2013.01); *H05B 3/46* (2013.01); *A61M 2016/0024* (2013.01); *A61M 2016/0027* (2013.01); *A61M 2205/13* (2013.01); *A61M 2205/3653* (2013.01); *A61M 2205/50* (2013.01); *A61M 2205/584* (2013.01); *A61M 2205/8206* (2013.01)

(58) Field of Classification Search
CPC ........ A24F 47/008; A24F 13/12; A24F 13/04; A61M 11/00; A61M 11/042; A61M 15/06; A61M 15/0068; A61M 15/008; A61M 15/0013; A61M 11/002
See application file for complete search history.

(56) References Cited

U.S. PATENT DOCUMENTS

| 4,557,888 A | * | 12/1985 | Rausing | B29C 33/505 156/203 |
| 5,865,186 A | * | 2/1999 | Volsey, II | A24F 47/006 131/194 |

(Continued)

FOREIGN PATENT DOCUMENTS

| CN | 103285488 A | 9/2013 |
| DE | 202013105420 U1 | 4/2014 |

(Continued)

OTHER PUBLICATIONS

Holman et al., "Chinese Pharmacist's E-Cigarette Drags Reynolds Into Vaping War", published on Jul. 12, 2016; retrieved online Jul. 13, 2016, at www.bloomberg.com/news/articles/2016-07-12/reynolds-imperial-fight-over-chinese-inventor-s-vape-patents.

(Continued)

*Primary Examiner* — Seyed Masoud Malekzadeh
*Assistant Examiner* — Taryn Trace Willett
(74) *Attorney, Agent, or Firm* — Dergosits & Noah LLP

(57) ABSTRACT

Handheld vaporizing devices with improved heating element and temperature controls, improved e-liquid reservoir, and capacitive technology to activate the heating element to prime the device to deliver aerosol on demand.

18 Claims, 2 Drawing Sheets

(51) Int. Cl.
*H05B 1/02* (2006.01)
*H05B 3/46* (2006.01)
*A61M 15/06* (2006.01)
*A61M 11/04* (2006.01)
*A61M 16/00* (2006.01)

(56) References Cited

U.S. PATENT DOCUMENTS

| | | | | |
|---|---|---|---|---|
| 5,894,841 | A * | 4/1999 | Voges | A24F 47/008 128/200.14 |
| 8,365,742 | B2 | 2/2013 | Hon | |
| 8,393,331 | B2 | 3/2013 | Hon | |
| 8,511,318 | B2 * | 8/2013 | Hon | A24F 47/002 128/202.21 |
| 8,528,569 | B1 | 9/2013 | Newton | |
| 8,781,307 | B2 * | 7/2014 | Buzzetti | A61M 11/041 392/386 |
| 9,635,887 | B2 * | 5/2017 | Ivey | A61L 9/122 |
| 2004/0069303 | A1 * | 4/2004 | Brown | A61M 15/0065 128/203.15 |
| 2007/0125371 | A1 * | 6/2007 | Djupesland | A61M 15/00 128/200.14 |
| 2009/0126723 | A1 * | 5/2009 | Dhuper | A61M 16/08 128/200.21 |
| 2011/0097060 | A1 | 4/2011 | Michael Buzzetti | |
| 2011/0265806 | A1 * | 11/2011 | Alarcon | A24F 47/00 131/273 |
| 2011/0309157 | A1 * | 12/2011 | Yang | A01M 1/2077 239/6 |
| 2011/0315152 | A1 | 12/2011 | Hearn | |
| 2012/0291791 | A1 * | 11/2012 | Pradeep | A24F 47/008 131/273 |
| 2012/0310185 | A1 * | 12/2012 | Defemme | A61F 9/0008 604/296 |
| 2013/0199528 | A1 * | 8/2013 | Goodman | F22B 1/282 128/203.26 |
| 2013/0220314 | A1 * | 8/2013 | Bottom | A61M 16/01 128/200.14 |
| 2013/0255702 | A1 * | 10/2013 | Griffith, Jr. | A24F 47/008 131/328 |
| 2013/0276781 | A1 * | 10/2013 | Steelman | A61M 15/0086 128/203.12 |
| 2014/0000638 | A1 * | 1/2014 | Sebastian | A24F 47/008 131/328 |
| 2014/0069424 | A1 * | 3/2014 | Poston | A24F 47/008 128/202.21 |
| 2014/0109899 | A1 * | 4/2014 | Boucher | A61M 11/06 128/200.18 |
| 2014/0190496 | A1 * | 7/2014 | Wensley | A24F 47/008 131/273 |
| 2014/0238423 | A1 * | 8/2014 | Tucker | A24F 47/008 131/328 |
| 2014/0270727 | A1 * | 9/2014 | Ampolini | A24F 47/008 392/387 |
| 2014/0338680 | A1 * | 11/2014 | Abramov | A24F 47/008 131/328 |
| 2015/0027470 | A1 * | 1/2015 | Kane | A24F 47/008 131/329 |
| 2015/0272216 | A1 * | 10/2015 | Dai | A61M 15/06 131/328 |
| 2016/0030687 | A1 * | 2/2016 | Engelbreth | A61M 15/0086 128/200.23 |
| 2016/0235120 | A1 * | 8/2016 | Liu | A24F 47/008 |
| 2016/0295922 | A1 * | 10/2016 | John | A24F 47/008 |
| 2016/0324216 | A1 * | 11/2016 | Li | A24F 47/008 |
| 2016/0338410 | A1 * | 11/2016 | Batista | A24F 47/008 |
| 2016/0345629 | A1 * | 12/2016 | Mironov | A24F 47/008 |
| 2016/0360785 | A1 * | 12/2016 | Bless | H05B 1/0244 |
| 2017/0035113 | A1 * | 2/2017 | Thorens | A24F 47/008 |
| 2017/0086502 | A1 * | 3/2017 | Hearn | A24F 47/008 |
| 2017/0196265 | A1 * | 7/2017 | Liu | A24F 47/008 |
| 2017/0196271 | A1 * | 7/2017 | Levitz | A24F 47/008 |
| 2017/0208863 | A1 * | 7/2017 | Davis | A24F 47/008 |

FOREIGN PATENT DOCUMENTS

| | | |
|---|---|---|
| JP | 58502192 A | 12/1983 |
| JP | 08511966 A | 12/1996 |
| WO | WO2014066730 A1 | 5/2014 |

OTHER PUBLICATIONS

International Search Report and Written Opinion for co-pending PCT Application No. PCT/US2015/031978; dated Aug. 18, 2015.
Series 100 Cartridge Check Valve, retrieved from http://www.smartproducts.com/check_valves_series_100_cartridge.php, retrieved on Jun. 15, 2017, 2 pages.
Saati Printing Bopp Wire, Printing Mesh, retrieved from http://www.saati.com/bopp-wire.php, retrieved on Jun. 15, 2017, 1 page.
Texas Instruments, Inc., Add some color to your design with TI's RGB and white LED drivers, retrieved from http://www.ti.com/lsds/ti/power-management/indicator-rgbw-overview.page, retrieved on Jun. 15, 2017, 6 pages.
Microban, Microguard Antifungal Protection retrieved from https://www.microban.com/micro-prevention/technologies/microguard, retrieved on Jun. 16, 2017, 6 pages.
Microban, Silvershield Technology, retrieved from https:/www.microban.com/micro-prevention/silvershield, retrieved on Jun. 16, 2017, 6 pages.
Microban, Zptech, Effective against bacteria, mold and mildew, retrieved from https:/www.microban.com/micro-prevention/technologies/zptech, retrieved Jun. 16, 2017, 6 pages.
Supplementary European Search Report related to EP Application No. 15795447.0, dated Dec. 13, 2017.
Notice of Reasons for Rejection for JP2017-513611, dated Apr. 9, 2019, 3 pages.
Abstract for JP08511966, Dec. 17, 1996, 2 pages.
Abstract for JP580502196, Dec. 22, 1983, 1 page.
Search Report for Taiwan Invention Patent Application No. 104116508, 1 page dated Jan. 30, 2019, 1 page.
Abstract for CN103285488, Sep. 9, 2013, 2 pages.

* cited by examiner

HANDHELD VAPORIZING DEVICE

CROSS REFERENCE TO RELATED APPLICATIONS

This application claims priority to U.S. Provisional Patent Application No. 62/001,972, entitled "E-Cigarette", filed on May 22, 2014, fully incorporated by reference herein.

FIELD OF THE INVENTION

The present invention relates to handheld vaporizing devices with improved heating element and temperature controls, improved e-liquid reservoir, and capacitive technology to activate the heating element to prime the device to deliver aerosol on demand.

BACKGROUND

Traditional handheld vaporizing devices, also known as e-cigarettes, are battery-operated portable devices comprising a battery, an atomizer, and an e-liquid cartridge. Handheld vaporizing devices are designed to deliver nicotine by producing an aerosol as a result of vaporizing a liquid solution known as an e-liquid. E-liquids usually contain a mixture of propylene glycol, vegetable glycerin, nicotine, and flavorings, while others release a flavored vapor without nicotine.

Traditional handheld vaporizing devices generally use a heating element known as an atomizer that vaporizes e-liquid to produce a nicotine aerosol for inhalation. An atomizer consists of a heating element responsible for vaporizing e-liquid and wicking material that draws the e-liquid from the cartridge. A heating element in the form of a resistance wire is coiled around the wicking material and is connected to a power source. The e-liquid is absorbed into the wicking material by capillary action. When the device is activated, the heating coil heats up and vaporizes the e-liquid that has been absorbed by the wicking material, creating the aerosol for inhalation.

Some prior art handheld vaporizing devices use a cartomizer, which is a device consisting of an atomizer and a cartridge integrated into a single component that connects to a power source. Prior art atomizer or cartomizer heating elements do not accurately control the heating and vaporization process. Significant variation in the quality and consistency of the wrapping of the heating wire around the wicking material, the differences in the electrical resistance of the wire, and the differences in the efficiency and absorption characteristics of the wicking material greatly affect the quantity or volume of the aerosol and the perceived quality of the aerosol that will be produced by the atomizer. Lack of temperature control may result in uneven heating and overheating of the heating element, which in turn may result in creation of hazardous chemicals in the vapor. For example, overheating of the e-liquid may result in creation of formaldehyde, inhalation of which is hazardous to the user's health.

In prior art handheld vaporizing devices, a user needed to inhale air through the device to activate the heating elements of the device in order to vaporize the e-liquid. It may take a user several puffs on the prior art device before it will generate sufficient vapor, resulting in inefficiency and inconvenience to the user.

The present invention is directed to overcome the drawbacks of the prior art by providing a novel handheld vaporizing devices incorporating an electroconductive textile heating element, e-liquid reservoir made of elastically deformable materials, and improved temperature and heating control system including an auto-on feature to prime the device to deliver aerosol on demand by activating the heating element upon sensing the user's touch on the device, without waiting for the user to take the first inhale through the device. The electroconductive textile heating element according to the present invention replaces the prior art wick and coils atomization systems and draws e-liquid by capillary action, and allows more even and direct heating of the e-liquid than traditional wicking systems.

DETAILED DESCRIPTION

A handheld vaporizing device according to an embodiment of the present invention will now be described with reference to FIGS. 1-3.

Figure 1:
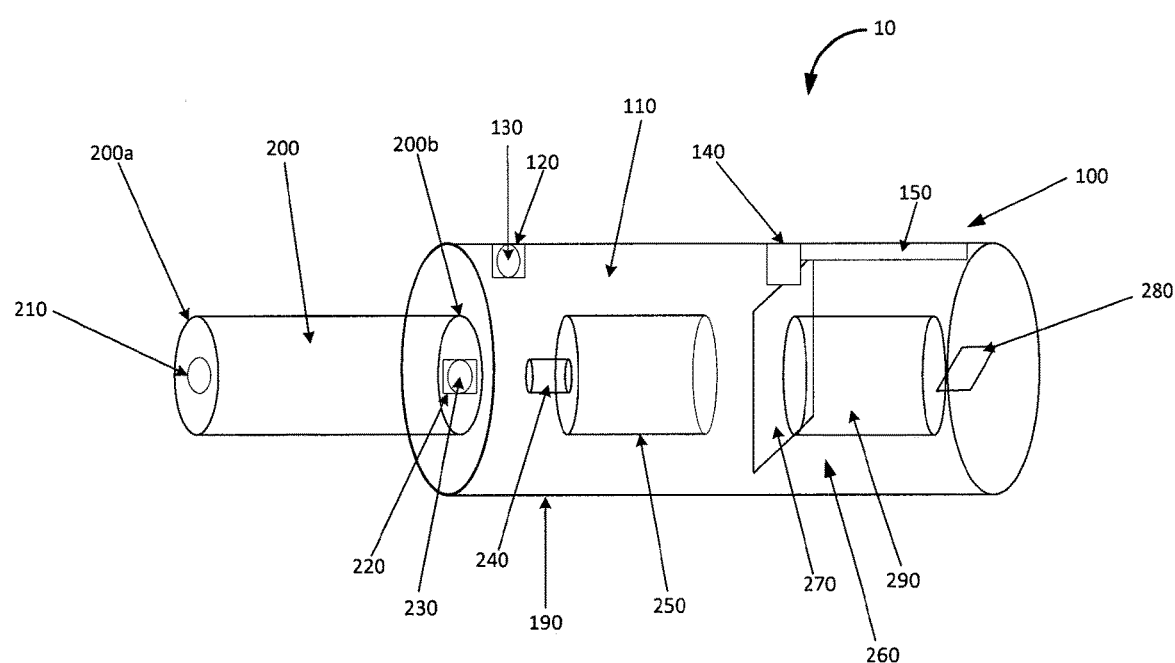
FIG. 1 is a top plan view of a handheld vaporizing device according to an embodiment of the present invention.

FIG. 1 illustrates a handheld vaporizing device 10 having a longitudinal axis and comprising a first and second longitudinal ends in oppositely-disposed first and second longitudinal directions. Handheld vaporizing device 10 comprises a mouth piece 200 and a main body 100. Main body 100 defines an interior cavity 110. A heating element 240, a reservoir 250, a power unit 260 comprising control circuitry 270 and power source 290, and a power connect element 280 are sequentially provided inside cavity 110.

A mouth piece 200, adapted to be held between the lips of a user, and having a first end 200a and a second end 200b, is connected to the first longitudinal end of body 100. In a preferred embodiment, mouth piece 200 is annular-shaped and comprises an inner shell of hard material such as, for example, metal or plastic, and an outer shell of soft pliable material such as, for example, foam, silicone or rubber, to mimic the feel of the filter of a conventional cigarette. Mouthpiece 200 may also include an anti-microbial agent coating to inhibit bacterial growth. Commercially available antimicrobial products such as, for example, Microban (http://www.microban.com/), or another comparable supplier, may be used according to methods known in the art.

Opening 210 is provided at end 200a of the mouth piece 200 to allow the aerosol to be drawn out of device 10 and into the user's lungs when a user applies an inhale portion of the user's breath to mouth piece 200. In a preferred embodiment, opening 210 has a generally circular cross section 1 mm to 1.5 cm in diameter. In other embodiments, opening 210 may have a square, triangular or any other geometric cross section shape.

Opening 230 is provided at the opposite end 200b of the mouth piece 200 to allow the aerosol to enter the mouth piece 200 when the user inhales. In a preferred embodiment, opening 230 has a generally circular cross section 1 mm to 1.5 cm in diameter. In other embodiments, opening 230 may have a square, triangular or any other geometric cross section shape.

Preferably, an air inlet check valve 220 is provided for opening and closing opening 230. Air inlet check valve 220 may be a commercially available product from, for example, Smart Products, Inc., (http://www.smartproducts.com/check_valves_series_100_cartridge.php), or another comparable supplier. In a preferred embodiment, a Series 100 Cartridge Check Valve (found at http://www.smartproducts.com/check_valves_series_100_cartridge.php) may be used.

Check valve 220 prevents environmental air from entering the interior of body 100 through openings 210 and 230 when device 10 is not in use, in order to prevent evaporation and oxidation of the e-liquid and to maintain e-liquid freshness. In addition, valve 220 prevents leakage of e-liquid out of the device, and keeps dust and dirt out of the device when carried in the user's pocket, bag, purse, etc.

A power connect element 280 is disposed in the second, opposite longitudinal end of body 100. In a preferred embodiment, the power connect element 280 comprises a Universal Serial Bus (USB) interface for insertedly connecting with an external power source, in order to allow the user to utilize universal chargers to charge device 10 without any adapters or chargers made especially for e-cigarettes. In other embodiments, the power connect element 280 may comprise a mini USB interface, a micro USB interface, or any other suitable communications bus known in the art.

Cavity 110 includes a power element 260 electrically coupled to the power connect element 280. Power element 260 comprises microprocessor control circuitry 270 and a power source 290. According to an embodiment of the invention, the power source may be a lithium polymer battery.

Cavity 110 includes an e-liquid reservoir 250, which may be either refillable or disposable. Reservoir 250 may be made of elastically deformable materials such as polymers or metal/polymer composites known in the art. According to an embodiment of the invention, reservoir 250 may be made of polyester with aluminum printed exterior and may be at least 5 ml in volume. This material is inert and keeps the external environmental factors from interacting with the liquid contents of the reservoir. An elastically deformable reservoir will allow the user to insert different types of e-liquids into the device, and will also allow the e-liquid to be fully utilized by the device, which provides an advantage over prior art devices with rigid reservoirs where some of the fluid remaining in the reservoir cannot reach the wick to be utilized.

Cavity 110 further includes a heating element 240 which is fluidly coupled to reservoir 250 and electrically coupled to power element 260. The heating element 240 according to this invention comprises an electroconductive textile heating element. The electroconductive textile heating element according to present invention include heating elements made of fabric with metalized or electro-conductive coating, fabric incorporating woven metal strands, or any other suitable materials known in the art. According to an embodiment of the invention, ultra thin grade stainless steel wire cloth (found at http://www.saati.com/bopp-wire.php or from another similar supplier may be used) may be used, and may be layered to form a sponge or a multi-ply electro-textile cloth. According to an embodiment of the invention, the finest mesh material Bopp stainless steel wire cloth having a 400 threads/inch may be used to ensure fast and even heating of the e-liquid.

The e-liquid reaches the electroconductive textile heating element via capillary action and is vaporized by the heating action of the electroconductive textile heating element. By providing an a electroconductive textile heating element coupled with a heating and temperature control system, the e-cigarette according to the invention allows an optimal vaporization state to be consistently maintained constantly so as to minimize or eliminate transformation of the e-liquid into unwanted chemicals such as formaldehyde.

An air opening 130 is disposed on the outer surface of body 100 between the first longitudinal end of body 100 and a position on the outer surface of body 100 corresponding to the location of the heating element 240 inside cavity 110. In a preferred embodiment, opening 130 has a generally circular cross section 1 mm to 1.5 cm in diameter. In other embodiments, opening 130 may have a square, triangular or any other geometric cross section shape. Other embodiments may comprise multiple air openings 130. In order to ensure that the air entering the device is moving at a sufficiently high velocity to allow for air mixing in the area surrounding the electroconductive textile heating element, the total cross-area of opening 130 should be less than the total cross-area of opening 230.

Preferably, an air inlet check valve 120 is provided for opening and closing each opening 130. Air inlet check valve 120 prevents environmental air from entering cavity 110 when e-cigarette 10 is not in use, to prevent evaporation and/or oxidation of the e-liquid. Air inlet check valve 120 may be a commercially available product from, for example, Smart Products, Inc., (http://www.smartproducts.com/check_valves_series_100_cartridge.php), or another comparable supplier. In a preferred embodiment, a Series 100 Cartridge Check Valve (found at http://www.smartproducts.com/check_valves_series_100_cartridge.php) may be used. In another embodiment, an elastic soft polymer flap attached to body 100 may be used in place of air inlet check valve 120. The opening pressure necessary to open either the air inlet check valve 120 or an elastic soft polymer flap should be reduced to a minimum (for example, 0.5 PSI) to allow the user to inhale effortlessly.

When the user inhales, he or she creates an area of negative pressure in mouth piece 200. The opening pressure necessary to open either the air inlet check valve 120 or an elastic soft polymer flap should be reduced to a minimum (for example, 0.5 PSI) to allow the user to inhale effortlessly. User's inhalation causes a pressure sensor switch located at the mouthpiece of the device to turn on the device and activate the heating element 240 by applying an electrical current from power element 260, thereby vaporizing some of the e-liquid and producing the aerosol mist. The negative pressure created by the user's inhale causes valves 120 and 220 to open, thereby allowing external air to enter cavity 110 through the opening 130. The aerosol mist then combines with the external air and passes through the mouth piece 200 to enter the user's lungs through the opening 210.

An LED element 140 (comprising an LED light and an LED driver), and a light channel 150 are disposed on the upper outer surface of body 100, and are electrically connected to the power element 260. According to another embodiment of the invention, a commercially available microprocessor with a build-in LED driver from Texas Instruments, Inc. (http://www.ti.com/lsds/ti/power-management/indicator-rgbw-overview.page) or from another similar supplier may be used.

According to an embodiment of the invention, the LED element 140 channels light via channel 150 along the upper surface of body 100 so as to make the light visible to the user. According to other embodiments, LED element 140 may be incorporated into second longitudinal end of body 100, opposite to the first end of body 100 which incorporates mouthpiece 200. LED light 140 may be activated by microprocessor control circuitry 270 when the user inhales from the e-cigarette. The intensity of the LED light is controlled by the microprocessor circuitry and by a pressure sensor located at the mouthpiece, according to methods known in the art. As the pressure sensor switch senses higher negative pressure caused by the user's inhale, it cause the microprocessor circuitry 270 to send a higher duty cycle to the LED element 140. A duty cycle is the ratio of time a circuit is ON to the time a circuit is OFF.

LED light 140 and light channel 150 may display various colors and flashing sequences of lights to denote dosage, battery level or other functional parameters of e-cigarette 10. The color or the intensity of the light may gradually change during usage of e-cigarette 10 to indicate the equivalent dosage of nicotine relative to a conventional cigarette that the user has inhaled. For example, light sequences may be "green" for full battery charge, "yellow" for about half charge, and "red" when the battery requires re-charge. Similar color schemes may be employed to indicate the amount of e-liquid remaining in the device.

Figure 2:
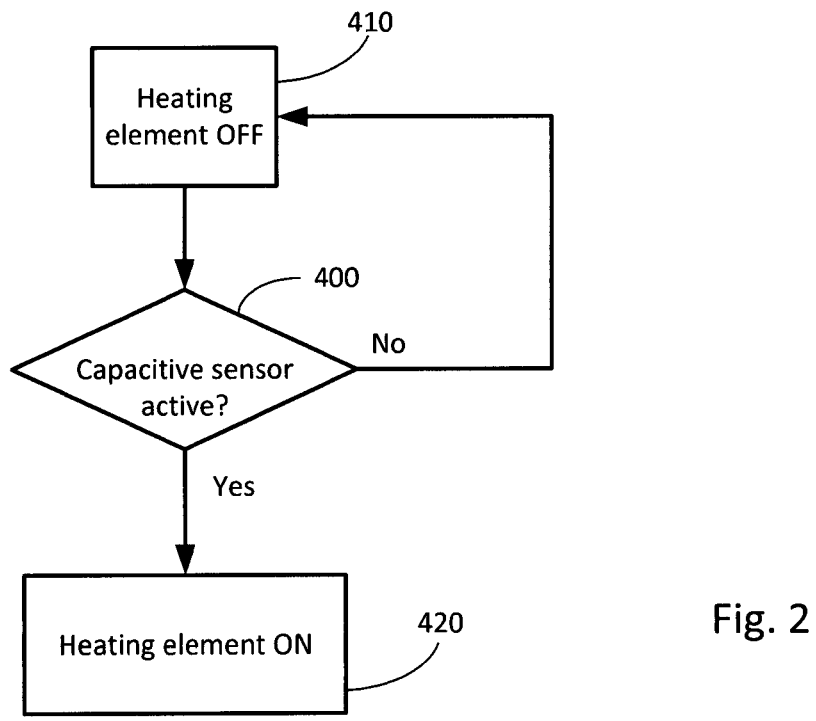
FIG. 2 illustrates the operation of the heating and temperature control system according to an embodiment of the present invention.

FIG. 2 illustrates the operation of the "auto-on" system to control the heating element 240 of a handheld vaporizing device 10 according to the present invention. Handheld vaporizing device 10 incorporates a capacitive touch sensor element 190. Capacitive touch sensor element 190 may be incorporated into body 100 of device 10, as illustrated in FIG. 1. According to other embodiments, capacitive touch sensor element 190 may be incorporated into the mouth piece 200 of device 10.

A step 400 of FIG. 2, the software and hardware of the microprocessor control circuitry 270 determines, according to the methods known in the art, if the capacitive sensor 190 is active or inactive. When capacitive touch sensor element 190 is active because the user is touching device 10, heating element 240 is turned on, as illustrated in step 420, and vapor is created by the vaporizing action of the heating element 240, thereby allowing the user to enjoy the vapor on demand. When capacitive touch sensor element 190 is inactive because the user is not touching device 10, heating element 240 is turned off, as illustrated in step 410 of FIG. 2.

Figure 3:
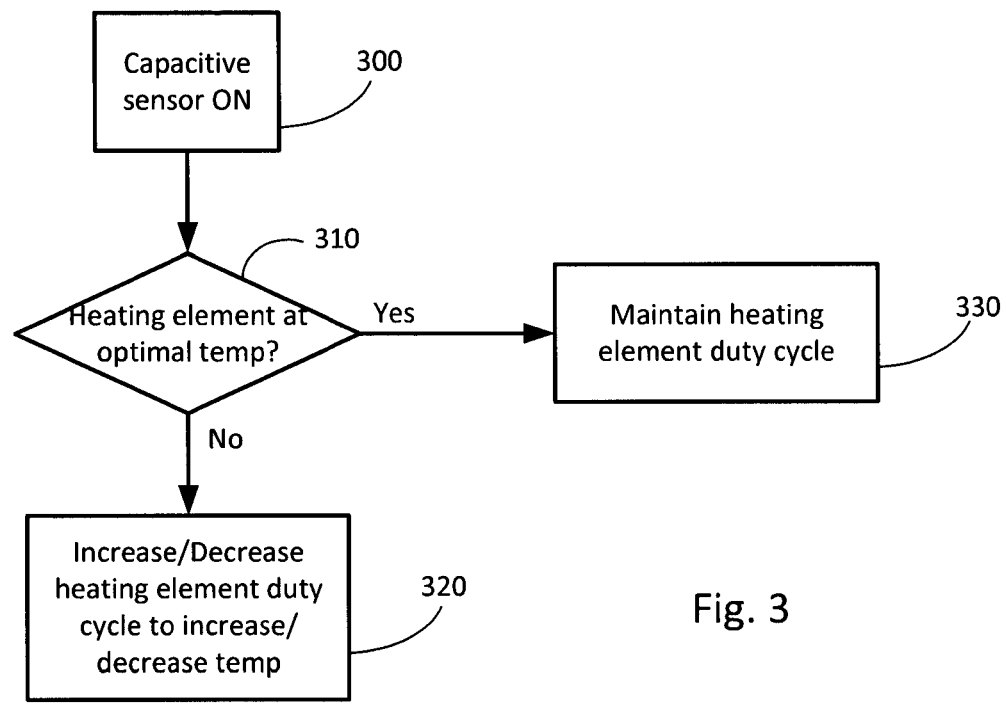
FIG. 3 illustrates the operation of the "auto-on" system according to an embodiment of the present invention.

FIG. 3 illustrates the operation of the heating and temperature control system to control the heating duty cycles of the heating element 240 according to the present invention. As shown in step 300 of FIG. 3, when the capacitive sensor 190 is active because the user is touching device 10, heating element 240 is activated and its duty cycles are controlled by the microprocessor control circuitry 270, to heat the e-liquid to an optimal pre set vaporization temperature of the e-liquid. This allows aerosol to be created when the user touches the device, without waiting for the user's first inhale. Thus, aerosol may be consumed immediately without the user having to take one or more puffs on the device to create the first dose of aerosol, thereby more closely mimicking the experience of smoking a real cigarette or cigar. As illustrated in step 310, the heating element is controlled by the microprocessor control circuitry 270 by methods known in the art not to significantly exceed or fall below the pre-set optimal vaporization temperature, assuring a supply of vapor and preventing generation of unwanted by-products of overheating the e-liquid. According to an embodiment of the invention, the heating element should be controlled not to exceed 120° C. to prevent formation of formaldehyde.

As illustrated in step 320 of FIG. 3, if the temperature of the heating element 240 falls above or below the optimal pre set vaporization temperature of the e-liquid, the duty cycles of the heating element 240 are increased or decreased by the microprocessor control circuitry 270 to maintain the temperature of the heating element 240 at optimal pre set vaporization temperature of the e-liquid.

The above mentioned is only exemplary embodiments of the present invention. It should be noted, for persons of ordinary skill in this art field, improvements and modifications within the spirit of the present invention can be further made, and such improvements and modifications should be seemed to be included in the claimed scope of the present invention.

What is claimed is:

1. A handheld electronic vaporizing device, comprising:
   a body defining a first cavity;
   a mouthpiece connected to said body, said mouthpiece defining a second cavity;
   an electroconductive textile heating element;
   a deformable reservoir;
   a power element;
   a power connect element;
   a capacitive touch sensor element;
   a light element;
   a first opening and a first valve located on a wall of said body to provide for a flow of air directly into said first cavity, wherein said first valve is normally closed and is opened by said flow, wherein said flow includes only air as said flow passes into said first cavity, and wherein said first opening includes a first opening area and said flow upon passing through said first opening and said first valve directly into said first cavity has a first velocity;
   a second opening and a second valve connecting said first cavity and said second cavity, wherein said second valve is normally closed and is opened by said flow, wherein said flow passes from said first cavity through said second opening and said second valve and into said second cavity, wherein said flow causes said first valve and said second valve to be open at the same time, and wherein said second opening includes a second opening area greater than said first opening area and said flow after passing through said second opening has a second velocity, said first velocity being greater than said second velocity; and
   a third opening disposed through a wall of said mouthpiece, wherein said electroconductive textile heating element, said reservoir, said power element and said power connect element are disposed inside said first cavity, and wherein said first velocity of said flow contributes to mixing said flow with a vapor in a space adjacent to said electroconductive textile heating element.

2. A handheld electronic vaporizing device according to claim 1, wherein said deformable reservoir is formed from a material selected from the group consisting of polymers and metal/polymer composites.

3. A handheld electronic vaporizing device according to claim 2, wherein said deformable reservoir comprises polyester with aluminum printed exterior.

4. A handheld electronic vaporizing device according to claim 1, wherein said electroconductive textile heating element includes a fabric selected from the group consisting of fabric with metalized coating, fabric with electro-conductive coating, and fabric incorporating woven metal strands.

5. A handheld electronic vaporizing device according to claim 4, wherein said electroconductive textile heating element comprises ultra thin grade stainless steel wire cloth.

6. A handheld electronic vaporizing device according to claim 1, wherein said electroconductive textile heating element is electrically responsive to said capacitive touch sensor element.

7. A handheld electronic vaporizing device according to claim 1, wherein said electroconductive textile heating element is activated by a user's touch on said capacitive touch sensor element.

8. A handheld electronic vaporizing device according to claim 1, wherein said electroconductive textile heating element is regulated to heat a volatile e-liquid to a pre-set temperature.

9. A handheld electronic vaporizing device according to claim 8, wherein said pre-set temperature is a temperature of vaporization of said volatile e-liquid.

10. A handheld electronic vaporizing device according to claim 1, wherein said capacitive touch sensor element regulates duty cycles of said electroconductive textile heating element.

11. A handheld electronic vaporizing device according to claim 1, wherein said light element comprises an LED light.

12. A handheld electronic vaporizing device according to claim 1, wherein said light element is electrically responsive to said capacitive touch sensor element.

13. A handheld electronic vaporizing device according to claim 1, wherein said capacitive touch sensor element regulates duty cycles of said light element.

14. A method for drawing vapor from a handheld electronic vaporization device comprising a body defining a first cavity, a mouthpiece connected to said body, said mouthpiece defining a second cavity, an electroconductive textile heating element, a deformable reservoir containing volatile e-liquid, a power element, a power connect element, a capacitive touch sensor element, a light element, a first opening and a first valve located on a wall of said body to provide for a flow of air directly into said first cavity, wherein said first valve is normally closed and is opened by said flow, wherein said flow includes only air as said flow passes into said first cavity, and wherein said first opening includes a first opening area and said flow upon passing through said first opening and said first valve directly into said first cavity has a first velocity, a second opening and a second valve connecting said first cavity and said second cavity, wherein said second valve is normally closed and is opened by said flow, wherein said flow passes from said first cavity through said second opening and said second valve and into said second cavity, wherein said flow causes said first valve and said second valve to be open at the same time, and wherein said second opening includes a second opening area greater than said first opening area and said flow after passing through said second opening has a second velocity, said first velocity being greater than said second velocity, and a third opening disposed through a wall of said mouthpiece, wherein said electroconductive textile heating element, said reservoir, said power element and said power connect element are disposed inside said first cavity, and wherein said first velocity of said flow contributes to mixing said flow with a vapor in a space adjacent to said electroconductive textile heating element, the method comprising:
supplying electrical power to said electroconductive textile heating element; heating said volatile e-liquid to a pre-set temperature;
creating an area of negative pressure external to said second cavity, said negative pressure causing said flow to pass from an exterior of said body through said first opening and said first valve, combine with vaporized e-liquid in said space adjacent to said electroconductive textile heating element, and continue to pass from said first cavity to said second opening, said second valve, said second cavity and through said third opening.

15. A method according to claim 14, wherein said pre-set temperature is a temperature of vaporization of said volatile e-liquid.

16. A handheld electronic vaporizing device according to claim 1 further comprising: a pressure sensor element disposed within said first cavity or said second cavity; and a processor and memory, said memory including instructions, said processor connected to receive a pressure signal from said pressure sensor element and connected to control said light element, wherein said light element is disposed on a surface of said body, wherein said processor is disposed inside said first cavity, and wherein said instructions, when executed by said processor cause said processor, during an activation of said handheld electronic vaporizing device, to:
determine a delivered dose of a compound based on said pressure signal,
determine a relative dose of said compound by comparing said delivered dose to a standard dose of said compound, and
control said light element based on said relative dose such that said light element changes during said activation to indicate a level of said relative dose, said level indicated by a change in said light element of at least one of a change in intensity of said light element and a change in color of said light element.

17. A handheld electronic vaporizing device, comprising:
a body defining a first cavity;
a mouthpiece connected to said body, said mouthpiece defining a second cavity;
an electroconductive textile heating element;
a deformable reservoir;
a power element;
a power connect element;
a pressure sensor element disposed within said first cavity or said second cavity;
a light element disposed on a surface of said body;
a processor and memory, said memory including instructions, said processor connected to receive a pressure signal from said pressure sensor element and connected to control said light element;
a first opening and a first valve located on a wall of said body, wherein said first valve is normally closed and is opened by a flow through said first opening and said first valve and into said first cavity;
a second opening and a second valve connecting said first cavity and said second cavity, wherein said second valve is normally closed and is opened by said flow passing from said first cavity through said second opening and said second valve and into said second cavity, said flow causing said first valve and said second valve to be open at the same time; and
a third opening disposed through a wall of said mouthpiece, wherein said electroconductive textile heating element, said reservoir, said power element, said processor, and said power connect element are disposed inside said first cavity, wherein said instructions, when executed by said processor cause said processor, during an activation of said handheld electronic vaporizing device, to:

determine a delivered dose of a compound based on said pressure signal, determine a relative dose of said compound by comparing said delivered dose to a standard dose of said compound, and control said light element based on said relative dose such that said light element changes during said activation to indicate a level of said relative dose, said level indicated by a change in said light element of at least one of a change in an intensity of said light element and a change in a color of said light element.

18. A handheld electronic vaporizing device according to claim 17,
wherein said first opening and said first valve are located on the wall to provide for the flow to flow directly into said first cavity;

wherein said flow includes only air as said flow passes into said first cavity, wherein said first opening includes a first opening area and said flow upon passing through said first opening and said first valve directly into said first cavity has a first velocity, wherein said second opening includes a second opening area greater than said first opening area and said flow, after passing through said second opening, has a second velocity, said first velocity being greater than said second velocity, and wherein said first velocity of said flow benefits a mixing of said flow with a vapor in a space adjacent to said electroconductive textile heating element.

* * * * *